United States Patent [19]

Obsumi et al.

[11] Patent Number: 5,525,632
[45] Date of Patent: Jun. 11, 1996

[54] STILBENE DERIVATIVES AND PHARMACEUTICAL COMPOSITIONS CONTAINING THEM

[75] Inventors: Koji Obsumi; Takashi Tsuji; Yoshihiro Morinaga; Kazuo Ohishi, all of Kawasaki, Japan

[73] Assignee: Ajinomoto Co., Ltd., Tokyo, Japan

[21] Appl. No.: 302,210

[22] Filed: Sep. 8, 1994

[30] Foreign Application Priority Data

Sep. 8, 1993 [JP] Japan ................................ 5-223573
Dec. 21, 1993 [JP] Japan ................................ 5-322832

[51] Int. Cl.$^6$ ..................... A61K 31/135; C07C 217/84
[52] U.S. Cl. ..................... 514/646; 514/523; 558/402; 564/443
[58] Field of Search ................... 558/402; 564/443; 514/523, 646

[56] References Cited

U.S. PATENT DOCUMENTS

5,081,251  1/1992  Bender et al. ................... 564/443
5,430,062  7/1995  Cushman et al. ................ 514/646

FOREIGN PATENT DOCUMENTS

WO93/23357  11/1993  WIPO.

OTHER PUBLICATIONS

Cushman, M. et al., "Synthesis and Evaluation of Stilbene and Dihydrostilbene Derivatives as Potential Anticancer Agents that Inhibit Tubulin Polymerization", Journal of Medicinal Chemistry, vol. 34, No. 8, 1991 pp. 2579–2588.
Cushman, M. et al., "Synthesis and Evaluation of Analogues of (Z)-1-(4-Methoxyphenyl)-2-(3,4,5-trimethoxyphenyl) ethene as Potential cytotoxic and antimitotic Agents", Journal of Medicinal History, vol. 35, No. 12, 1992, pp. 2293–2306.

Viel, C., Abstract No. 13525, Chemical Abstracts, vol. 79, No. 3, p. 21 (1973).

Hartmann et al., "Ring–Substituted 1,2–Dialkylated 1,2–Bis(hydroxyphenyl) ethanes. 2. Synthesis and Estrogen Receptor Binding Affinity of 4–4'–5,5', and 6,6'–Disubstituted Metahexestrols", Journal of Medicinal Chemistry, vol. 27, No. 5, 1984, pp. 577–585.

Stewart, J. T., "Synthesis and Biological Evaluation of substituted .alpha.–Phenylcinnamonitriles", Journal of Pharmaceutical Sciences, vol. 60, No. 8, 1971, pp. 1244–1245.

Olszewski et al, J. Org. Chem., vol. 59 (1994), pp. 4285–4296.

*Primary Examiner*—Richard L. Raymond
*Attorney, Agent, or Firm*—Sughrue, Mion, Zinn, Macpeak & Seas

[57] ABSTRACT

A stilbene derivative of the following general formula (I) or a pharmaceutically acceptable acid addition salt thereof have low toxicity, but are water soluble and effective as carcinostatics:

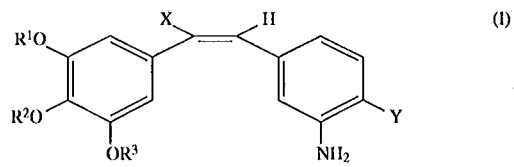

wherein $R^1$, $R^2$ and $R^3$, which may be the same or different, each represent an alkyl group having 1 to 3 carbon atoms; X represents a hydrogen atom or a nitrile group; Y represents an alkyloxy group having 1 to 3 carbon atoms, an alkyl group having 1 to 6 carbon atoms or a halogen atom.

6 Claims, No Drawings

STILBENE DERIVATIVES AND PHARMACEUTICAL COMPOSITIONS CONTAINING THEM

FIELD OF THE INVENTION

The present invention relates to cis-stilbene derivatives, to their use as pharmaceuticals and, in particular, to carcinostatics containing them as active ingredients.

BACKGROUND OF THE INVENTION

Combretastatins having cis-stilbene as their basic skeleton are known to have strong cytotoxicity. However, because they are barely soluble in water, they have not been put to practical use as medicines. Therefore, various investigations to develop derivatives of these compounds have been made (Molecular Pharmacology 34, 200-206 (1988); J. Med. Chem., 34, 2579-2588 (1991); WO 92/16486; J. Med. Chem., ,35, 2293-2306 (1992); WO 93/23357; J. Med. Chem., 36, 2817-2821 (1993); Bioorg. Med. Chem. Let., 4, 699-704 (1994)), but compounds, which are effective in vivo are still unknown.

SUMMARY OF THE INVENTION

The present inventors sought to identify combretastatin derivatives which may be synthesized easily, which have low toxicity and which have a high pharmaceutical effect, and to provide carcinostatics containing them.

The present inventors synthesized various stilbene derivatives and screened carcinostatic compounds from them. As a result, they have found that compounds of the following general formula (I) have a remarkable carcinostatic effect in vivo.

These compounds, which have an amino group at the 3-position of the benzene ring of cis-stilbene, are novel combretastatin derivatives.

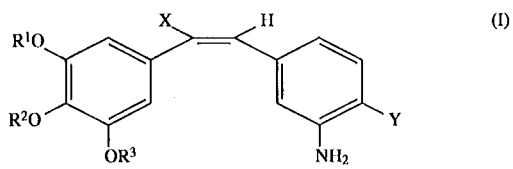

wherein $R^1$, $R^2$ and $R^3$, which may be the same or different, each represent an alkyl group having 1 to 3 carbon atoms; X represents a hydrogen atom or a nitrile group; Y represents an alkyloxy group having 1 to 3 carbon atoms, an alkyl group having 1 to 6 carbon atoms or a halogen atom.

DETAILED DESCRIPTION OF THE INVENTION

In formula (I), the term "an alkyl group having 1 to 3 carbon atoms" means methyl, ethyl and propyl; the term "an alkyl group having 1 to 6 carbon atoms" means methyl, ethyl, propyl, isopropyl, butyl, isobutyl, pentyl, hexyl and the like; the term "a halogen atom" means a fluorine atom, a chlorine atom, a bromine atom and an iodine atom.

In preferred compounds $R^1$, $R^2$ and $R^3$ are all methyl groups. Y is most preferably a methoxy group.

Exemplary compounds include, for example, the following:

(Z)-1-(3-amino-4-methoxyphenyl)-2-(3,4,5-trimethoxyphenyl) ethene, (Z)-1-(3-amino-4-chlorophenyl)-2-(3,4,5-trimethoxyphenyl) ethene, (Z)-1-(3-amino-4-methylphenyl)-2-(3,4,5-trimethoxyphenyl) ethene, (E)-3-(3-amino-4-methoxyphenyl)-2-(3,4,5-trimethoxyphenyl)-prop-2-en-nitrile, (E)-3-(3-amino-4-chlorophenyl )-2-(3,4,5-trimethoxyphenyl)-prop-2-en-nitrile, (E)-3-(3-amino-4-methyphenyl)-2-(3,4,5-trimethoxyphenyl-prop-2-en-nitrile.

Compounds of formula (I) of the present invention may be produced, for example, according to the reaction schemes described below.

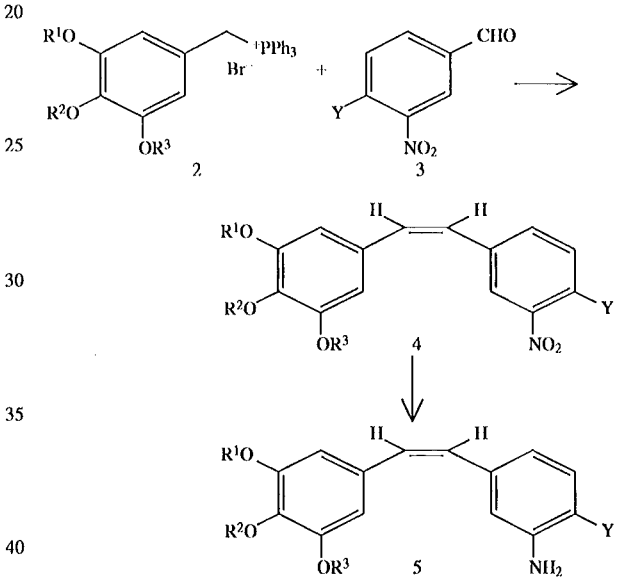

In these formulae, $R^1$, $R^2$, $R^3$ and Y have the same meanings as described above.

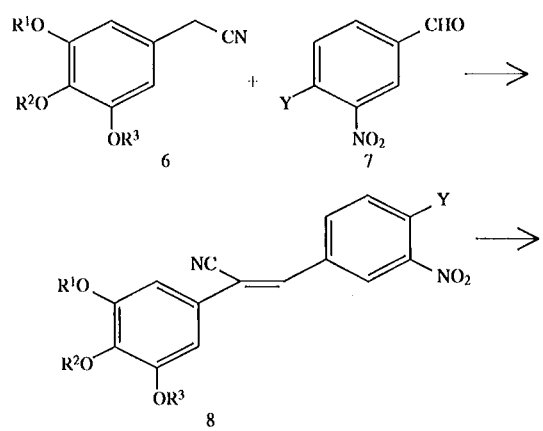

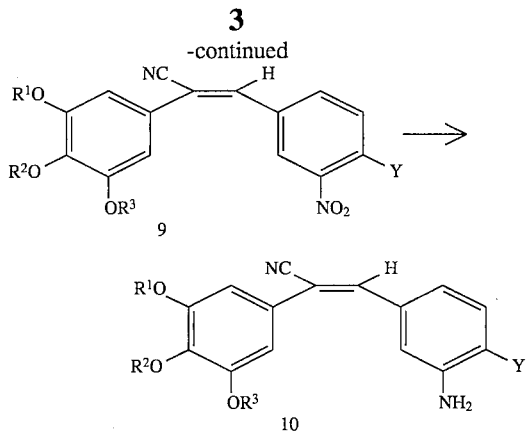

In these formulae, $R^1$, $R^2$, $R^3$ and Y have the same meanings as described above.

More specifically, compounds of formula (5) which belong to the compounds of the present invention may be obtained, for example, by reacting a triphenylphosphine bromide derivative of formula (2) and an aldehyde of formula (3) at room temperature in alcohol or benzene, etc. in the presence of a base such as sodium hydride or sodium ethoxide for 2 to 4 hours followed by subjecting the reaction product to chromatography, etc. to obtain the intended cis-compound. The cis-compound may be reduced with zinc-acetic acid or the like to obtain a compound of formula (5).

Compounds of formula (10) which belong to the compounds of the present invention may be produced, for example, by reacting a phenylacetonitrile derivative (6) and an aldehyde derivative (7) in dichloromethane, etc. in the presence of sodium hydroxide for 2 to 4 hours, obtaining the cis-compound (9) by photo-isomerizing the trans-compound (8) followed by reducing the cis-compound (9) with a reducing agent such as zinc-acetic acid.

The stilbene derivatives of the present invention that have been produced according to the above-mentioned method may easily be separated and purified from the reaction mixtures obtained using conventional isolation and purifying means, for example, by extraction with solvents, chromatography, crystallization, etc.

Where the above-described stilbene derivatives are used as carcinostatics, they are administered to patients perorally or parenterally (for example, by intramuscular injection, subcutaneous injection or intravenous injection or as suppositories, etc.). Their dose varies depending on the symptoms of patients. In general, a suitable dosage is from 1 to 9000 mg/adult/day and the dosage can be portions of from 1 to 3000 mg each to be administered to patients several times a day.

Where the stilbene derivatives of the present invention are formulated into peroral preparations, a vehicle and optionally other additives such as binder, disintegrator, lubricant, colorant, flavoring, etc. are added thereto and the resulting mixtures are formed into tablets, coated tablets, granules, capsules, etc. by ordinary methods. For example, lactose, corn starch, white sugar, glucose, sorbitol, crystalline cellulose, etc., are suitable as the vehicle. Polyvinyl alcohol, polyvinyl ether, ethyl cellulose, methyl cellulose, arabic gum, tragacanth, gelatin, shellac, hydroxypropyl cellulose, hydroxypropyl starch, polyvinyl pyrrolidone, etc., are suitable as a binder. The disintegrator, for example, can be starch, agar, gelatin powder, crystalline cellulose, calcium carbonate, sodium hydrogencarbonate, calcium citrate, dextran, pectin, etc. Typical lubricants, for example, are magnesium stearate, talc, polyethylene glycol, silica, hardened vegetable oils, etc. Exemplary colorants, for example, include colorants that have been accepted as those appropriate for medicines. As the flavoring, for example, usable are cocoa powder, menthol, aromatic acids, peppermint oil, borneol, cinnamon powder, etc. As a matter of course, these tablets and granules may optionally be coated, for example, with sugar coats, gelatin coats, etc.

Where the stilbene derivatives of the present invention are formulated into injections, a pH-adjusting agent, a buffer, a stabilizer, a preservative, etc. may optionally be added thereto and formed into subcantaneous, intramuscular or intravenous injections using conventional techniques.

The stilbene derivatives of the present invention may optionally be formed into their pharmaceutically-acceptable acid-addition salts with inorganic acids such as hydrochloric acid, sulfuric acid, phosphoric acid, etc. and with organic acids such as oxalic acid, fumaric acid, maleic acid, malic acid, citric acid, tartaric acid, glutamic acid, etc.

The present invention is explained in greater detail by means of the following examples, which, however, are not intended to be construed as restricting the scope of the present invention. Unless otherwise indicated herein, all parts, percents, ratios and the like are by weight.

EXAMPLE 1

Preparation of (Z)-1-(3-Amino-4-methoxyphenyl)-2-(3,4,5-trimethoxyphenyl) ethene Step 1: Preparation of (Z)-1-(3-nitro-4-methoxyphenyl)-2-(3,4,5-trimethoxyphenyl) ethene 1.54 g of 3-nitro-4-methoxybenzaldehyde and 4.45 g of 3,4,5-trimethoxybenzyltriphenylphosphine bromide were dissolved in 40 ml of benzene, and a benzene solution containing 408 mg of sodium hydride dispersed therein was added thereto and reacted for 15 hours at room temperature (about 20°–30° C.). The reaction mixture was neutralized with acetic acid, saturated sodium chloride solution was added thereto, and the resulting liquid was extracted with dichloromethane. The extract was dried with anhydrous sodium sulfate, concentrated and then purified by silica gel column chromatography (ethyl acetate:hexane=1:2 by volume) to obtain 1.27 g of the intended compound. The yield of the product was 43%.

$^1$-NMR(CDCl$_3$): 7.79 (1H, d, J=2.1), 7.42 (1H, dd, J-2.1, 8.7), 6.93 (1H, d, J=8.7), 6.58 (1H, d, J=12.9), 6.47 (2H, s), 6.44 (1H, d, J=12.9), 3.93 (3H, s), 3.85 (3H, s), 3.71 (6H, s); mass spectrum (m/z): 345 (M$^+$)

Step 2: Preparation of (Z)-1-(3 -amino-4-methoxyphenyl)-2-(3,4,5-trimethoxyphenyl) ethene 700 mg of (Z)-1-(3-nitro-4-methoxyphenyl)-2-(3,4,5-trimethoxyphenyl) ethene were dissolved in 35 ml of acetic acid, and 7 g of zinc were added thereto and stirred for one hour. The reaction liquid was filtered, concentrated and purified by silica gel column chromatography (dichloromethane: hexane=2:1 by volume) to obtain 314 mg of the intended compound. The yield was 49.3%.

$^1$H-NMR(CDCl$_3$): 6.69 (1H, s), 6.67 (2H, s), 6.55 (2H, s), 6.45 (1H, d, J=12.0), 6.36 (1H, d, J=12.0), 3.84 (3H, s), 3.82 (3H, s), 3.69 (6H, s); mass spectrum (m/z): 315 (M$^+$).

EXAMPLE 2

Preparation of (Z)-1-(3-amino-4-chlorophenyl)-2-(3,4,5 -trimethoxyphenyl) ethene Step 1: Preparation of (Z)-1-(3-nitro-4-chlorophenyl)-2-(3,4,5-trimethoxyphenyl) ethene 1.0 g of 3-nitro-4-chlorobenzaldehyde and 2.8 g of 3,4,5-trimethoxybenzyltriphenylphosphine bromide were dissolved in 50 ml of benzene, and a benzene solution containing 260 mg of sodium hydride dispersed therein was added thereto and reacted for 15 hours at room temperature. The reaction liquid was neutralized with acetic acid, saturated sodium chloride solution was added thereto, and the resulting liquid was extracted with dichloromethane. The extract was dried with anhydrous sodium sulfate, concentrated and then purified by silica gel column chromatography diethyl (ether:hexane—1:2 by volume) to obtain 0.95 g of the intended compound. The yield of the product was 50.4%.

$^1$H-NMR(CDCl$_3$): 7.79 (1H, s), 7.39 (2H, s), 6.70 (1H, d, J=12.0), 6.47 (1H, d, J=12.0), 6.44 (2H, s), 3.86 (3H, s), 3.72 (6H, s); mass spectrum (m/z): 349 (M$^+$)

Step 2: Preparation of (Z)-1-(3-amino-4-chlorophenyl)-2-(3,4,5-trimethoxyphenyl) ethene 85 mg of (Z)-1-(3-nitro-4-chlorophenyl)-2-(3,4,5-trimethoyphenyl) ethene were dissolved in 4 ml of acetic acid and 4 ml of dichloromethane, and 400 mg of zinc were added thereto and stirred for one hour. The reaction liquid was filtered, concentrated and purified by silica gel column chromatography (dichloromethane:hexane=2.1 by volume) to obtain 52 mg of the intended compound. The yield was 66.8%.

$^1$H-NMR(CDCl$_3$): 7.12 (1H, d, J=7.8), 6.71 (1H, d, J=1.8), 6.62 (1H, d, J=1.8, 7.8), 6.49 (2H, s), 6.45 (2H, s), 3.84 (3H, s), 3.69 (6H, s); mass spectrum (m/z): 319 (M$^+$)

EXAMPLE 3

Preparation of (Z)-1-(3-amino-4-methylphenyl)-2-(3,4,5-trimethoxyphenyl) ethene

Step 1: Preparation of (Z)-1-(3-nitro-4-methylphenyl)-2-(3,4,5-trimethoxyphenyl) ethene 1.0 g of 3-nitro-4-methylbenzaldehyde and 3.3 g of 3,4,5-trimethoxybenzyltriphenylphosphine bromide were dissolved in 50 ml of benzene, and a benzene solution containing 302 mg of sodium hydride dispersed therein was added thereto and reacted for 15 hours at room temperature. The reaction liquid was neutralized with acetic acid, saturated sodium chloride solution was added thereto, and the resulting liquid was extracted with dichloromethane. The extract was dried with anhydrous sodium sulfate, concentrated and then purified by silica gel column chromatography (diethyl ether:hexane=1:2 by volume) to obtain 0.99 g of the intended compound. The yield of the product was 47.8%.

$^1$H-NMR(CDCl$_3$): 7.89 (1H, d, J=1.8), 7.40 (1H, dd, J=1.8, 7.8), 7.19 (1H, d, J=7.8), 6.63 (1H, d, J=12.3), 6.50 (1H, d, J=12.3), 6.46 (2H, s), 3.85 (3H, s); 3.69 (6H, s), 2.55 (3H, s); mass spectrum (m/z): 329 (M$^+$)

Step 2: Preparation of (Z)-1-(3-amino-4-methylphenyl)-2-(3,4,5-trimethoxyphenyl) ethene 65 mg of (Z)-1-(3-nitro-4-methylphenyl)-2-(3,4,5-trimethoxyphenyl) ethene were dissolved in 4 ml of acetic acid and 4 ml of dichloromethane, and 300 mg of zinc were added thereto and stirred for one hour. The reaction liquid was filtered, concentrated and purified by silica gel column chromatography (dichloromethane:hexane=2.1 by volume) to obtain 29 mg of the intended compound. The yield was 46.5%.

$^1$H-NMR(CDCl$_3$): 6.93 (1H, d, J=7.5), 6.65 (1H, dd, J=1.8, 7.5), 6.63 (1H, d, J=1.8), 6.53 (2H, s), 6.49 (1H, d, J=12.3), 6.40 (1H, d, J=12.3), 3.83 (3H, s); 3.68 (6H, s), 2.13 (3H, s); mass spectrum (m/z): 299 (M$^+$)

EXAMPLE 4

Preparation of (E)-3-(3-amino-4-methoxyphenyl)-2-(3,4,5-trimethoxyphenyl)-prop-3-ene-nitrile Step 1: Preparation of (Z)-3-(3-nitro-4-methoxyphenyl)-2-(3,4,5-trimethoxyphenyl)-prop-2-ene-nitrile 3.0 g of 3-nitro-4-methoxybenzaldehyde, 3.4 g of 3,4,5-trimethoxyphenylacetonitrile, 800 mg of sodium hydroxide and 100 mg of octylmethylammonium chloride were dissolved in 15 ml of water and 15 ml of dichloromethane and reacted for 4 hours at room temperature. Ice water was added to the reaction liquid, which was then extracted three times each with dichloromethane. The extract was dried with anhydrous sodium sulfate and concentrated. The concentrated liquid was purified by crystallization (ethyl acetate) to obtain 4.4 g of the intended compound. The yield was 72%.

$^1$H-NMR(CDCl$_3$): 8.30 (1H, dd, J=2.4, J=9.0), 8.21 (1H, d, J=2.4), 7.38 (1H, s), 7.21 (1H, d, J=9.0), 6.86 (2H, s), 4.05 (3H, s), 3.94 (6H, s), 3.89 (3H, s); mass spectrum (m/z): 370 (M$^+$); melting point 191°–192° C.

Step 2: Preparation of (E)-3-(3-nitro-4-methoxyphenyl)-2-(3,4,5-trimethoxyphenyl)-prop-2-ene-nitrile 2.0 g of (Z)-3-(3-nitro-4-methoxyphenyl)-2-(3,4,5-trimethoxyphenyl)-prop-2-ene-nitrile were dissolved in 500 ml of acetonitrile and exposed to visible light rays for 60 minutes. The reaction liquid was concentrated and crystallized from ethyl acetate to obtain 996 mg of the intended compound. The yield was 49%.

$^1$H-NMR(CDCl$_3$): 7.74 (1H, d, J=2.1), 7.35 (1H, dd, J=2.1, 9.0), 7.19 (1H, s), 6.94 (1H, d, J=9.0), 6.58 (2H, s), 3.95 (3H, s), 3.89 (3H, s), 3.78 (6H, s); mass spectrum (m/z): 370 (M$^+$); melting point 158°–159° C.

Step 3: Preparation of (E)-3-(3-amino-4-methoxyphenyl)-2-(3,4,5-trimethoxyphenyl)-prop-2-ene-nitrile 500 mg of (E)-3-(3-nitro-4-methoxyphenyl)-2-(3,4,5-trimethoxyphenyl)-prop-2-ene-nitrile were dissolved in 25 ml of acetic acid, and 5 g of zinc were added thereto and stirred for 30 minutes at room temperature. The reaction liquid was filtered and then concentrated. The concentrated liquid was purified by silica gel column chromatography (ethyl acetate:hexane—1.2 by volume) to obtain 457 mg of the intended compound. The yield was 99%.

$^1$H-NMR(CDCl$_3$): 7.26 (1H, s), 6.65 (2H, s), 6.64 (1H, s), 6.56 (1H, s), 3.88 (3H, s), 3.84 (3H, s), 3.77 (6H, s); mass spectrum (m/z): 340 (M$^+$); melting point 144°–145° C.

EXAMPLE 5

Preparation of (E)-3-(3-amino-4-methylphenyl)-2-(3,4,5-trimethoxyphenyl)-prop-2-ene-nitrile Step 1: Preparation of (Z)-3-(3-nitro-4-methylphenyl)-2-(3,4,5-trimethoxyphenyl)-prop-2-ene-nitrile 5.0 g of 3-nitro-4-methylbenzaldehyde, 6.27 g of 3,4,5-trimethoxyphenylacetonitrile, 1.44 g of sodium hydroxide and 500 mg of trioctylmethylammonium chloride were dissolved in 25 ml of water and 500 ml of dichloromethane. The mixture was stirred vigorously for 3 hours at room temperature. The ice water was added to the mixture and the mixture was extracted with dichloromethane three times and dried over anhydrous sodium sulfate. The organic layer was concentrated and the residue was purified by silica gel column chromatography (dichloromethane) to give 1.5 g of the intended compound. The yield was 14.1%.

$^1$H-NMR(CDCl$_3$): 8.35 (1H, J=1.5), 8.18 (1H, dd, J=1.5, 8.1), 7.47 (1H, d, J=8.1), 7.44 (1H, s), 6.88 (2H, s), 3.95 (6H, s), 3.90 (3H, s), 2.67 (3H, s); mass spectrum (m/z): 354 (M$^+$); melting point 162°–163° C.

Step 2: Preparation of (E)-3-(3-nitro-4-methylphenyl)-2-(3,4,5-trimethoxyphenyl)-prop-2-ene-nitrile 1.38 g of (Z)-3-(3-nitro-4-methylphenyl)-2-(3,4,5-trimethoxyphenyl)-prop-2-ene-nitrile was dissolved in 500 ml of acetone and the mixture was reacted in a photochemical apparatus (visible light) for 1 hour. The reaction mixture was concentrated and a quarter of it was purified on a silica gel plate to give 100 mg of the intended compound.

$^1$H-NMR(CDCl$_3$): 7.84 (1H, d, J=1.8), 7.29 (1H, dd, J=1.8, 8.1), 7.26 (1H, s), 7.22 (1H, d, J=8.1), 6.56 (2H, s), 3.89 (3H, s), 3.75 (3H, s), 2.57 (3H, s); mass spectrum (m/z): 354 (M$^+$); melting point 169°–170° C.

Step 3: Preparation of (E)-3-(3-amino-4-methylphenyl)-2-(3,4,5-trimethoxyphenyl)-prop-2-ene-nitrile 84 mg of (E)-3-(3-nitro-4-methylphenyl)-2-(3,4,5-trimethoxyphenyl)-prop-2-ene-nitrile was dissolved in 8 ml of acetic acid then zinc was added to the mixture. The mixture was stirred vigorously for 1 hour then filtered and concentrated. The residue was purified on a silica gel plate (dichloromethane) to give 60 mg of the intended compound.

$^1$H-NMR(CDCl$_3$): 7.20 (1H, s), 6.92 (1H, d, J=7.5), 6.62 (2H,, s), 6.56 (1H, dd, J=0.9, 7.5), 6.51 (1H, s), 3.87 (3H, s), 3.75 (6H, s), 2.13 (3H, s); mass spectrum (m/z): 324 (M$^+$); melting point 161°–162° C.

EXAMPLE 6

Preparation of (E)-3-(3-amino-4-chlorophenyl)-2-(3,4,5-trimethoxyphenyl)-prop-2-ene-nitrile Step 1: Preparation of (Z)-3-(3-nitro-4-chlorophenyl)-2-(3,4,5-trimethoxyphenyl)-prop-2-ene-nitrile 5.0 g of 3-nitro-4-chlorobenzaldehyde, 5.6 g of 3,4,5-trimethoxyphenylacetonitrile, 1.3 g of sodium hydroxide and 500 mg of trioctylmethylammonium chloride were dissolved in 10 ml of water and 50 ml of dichloromethane. The mixture was stirred vigorously for 3 hours at room temperature. The ice water was added to the mixture and the mixture was extracted with dichloromethane three times and dried over anhydrous sodium sulfate. The organic layer was concentrated and the residue was crystallized from ethyl acetate to give 4.9 g of the intended compound. The yield was 48.5%.

$^1$H-NMR(CDCl$_3$): 8.23 (1H, J=2.1), 8.15 (1H, dd, J=2.1, 8.4), 7.67 (1H, d, J=8.4), 7.41 (1H, s), 6.88 (2H, s), 3.94 (6H, s), 3.91 (3H, s), mass spectrum (m/z): 374 (M$^+$); melting point 198°–199° C.

Step 2: Preparation of (E)-3-(3-nitro-4-chlorophenyl)-2-(3,4,5-trimethoxyphenyl)-prop-2-ene-nitrile:12

1.5 g of (Z)-3-(3-nitro-4-chlorophenyl)-2-(3,4,5-trimethoxyphenyl)-prop-2-ene-nitrile was dissolved in 500 ml of acetone and the solution was reacted in a photochemical apparatus (visible light) for 1 hour. The reaction mixture was concentrated and a half of it was purified on a silica gel plate to give 400 mg of the intended compound.

$^1$H-NMR(CDCl$_3$): 7.74 (1H, d, J=2.1), 7.44 (1H, d, J=8.7), 7.32 (1H, dd, J=2.1, 8.7), 7.23 (1H, s), 6.55 (2H, s), 3.89 (3H, s), 3.77 (6H, s), mass spectrum (m/z): 374 (M$^+$)

Step 3: Preparation of (E)-3-(3-amino-4-chlorophenyl)-2-(3, 4,5-trimethoxyphenyl)-prop-2-ene-nitrile (E)-3-(3-nitro-4-chlorophenyl)-2-(3,4,5-trimethoxyphenyl)-prop-2-ene-nitrile 330 mg was dissolved in 8 ml of acetic acid then zinc was added to the mixture. The mixture was stirred vigorously for one hour then filtered and concentrated. The residue was purified on a silica gel plate (dichloromethane) to give 102 mg of desired product (yield 33%).

$^1$H-NMR (CDCl$_3$): 7.17 (1H, s), 7.12 (1H, d, J=8.1), 6.61 (1H, d, J=1.8), 6.59 (2H, s), 6.53 (1H, dd, J=1.8, 8.1), 3.88 (3H, s), 3.75 (6H, s), mass spectrum 344 (M$^+$); melting point: 150°–151° C.

EXAMPLE 7

Cytotoxicity Testing

Mouse P388 leukemia cells were used as cancer cells for this test. The cancer cells were incubated in RPMI-1640 medium containing 5 μM 2-mercaptoethanol and 10% fetal calf serum. More specifically, the cancer cells were seeded in a 96-well microplate in an amount of 1×10$^4$ cell/50 μl/well, 25 μl/well of an aqueous solution of the test compound mentioned below (4 μg/ml) were added to each well, and the cells were incubated therein for 2 days at 37° C. After the incubation, the number of the living cells was counted using the MTT method and a dose-reaction curve was formed from the counted data. Based on the curve, the 50% growth-inhibiting concentration (IC$_{50}$) of the test compound was calculated. The IC$_{50}$ value of each compound obtained is shown in Table 1 below. As a comparative compound, Combretastatin A-4 was used. As is noted from Table 1, the compounds of the present invention each have IC$_{50}$ value comparable to that of Combretastatin A-4.

EXAMPLE 8

Evaluation of Antitumor Activity

Colon 26 was inoculated sc into CD2F1 mice. After a week, the size of the tumor was measured and the volume of the tumor was calculated. Mice were selected on the basis of the volume of the tumor and administration of drug was begun. Twenty-one days after the day of administration, the size of the tumor was measured and the volume of the tumor was calculated. The inhibition ratio of growth of tumor (I.R.) was calculated as shown below. I.R. (%) ={1-(Average Tumor Volume of Treated Mice)/(Average Tumor Volume of Control Mice)}×100

The inhibition ratios are shown in Table 1 below.

TABLE 1

| NAME OF COMPOUNDS | STRUCTURE | In vitro IC$_{50}$(ng/ml) | In vivo I.R. (%) |
|---|---|---|---|
| (Z)-1-(3-Amino-4-methoxy phenyl)-2-(3,4,5-trimethoxy phenyl)-ethene | CH$_3$O—(3,4,5-trimethoxyphenyl)—CH=CH—(3-amino-4-methoxyphenyl) | 0.2 | 69.5$^{a), c)}$ (40 mg/day) |

TABLE 1-continued

| NAME OF COMPOUNDS | STRUCTURE | In vitro IC$_{50}$(ng/ml) | In vivo I.R. (%) |
| --- | --- | --- | --- |
| (Z)-1-(3-Amino-4-chloro phenyl)-2-(3,4,5-trimethoxy phenyl)-ethene | 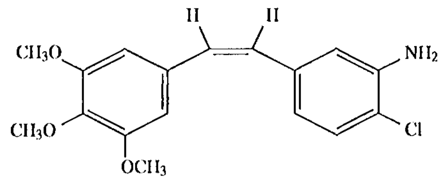 | 20 | NOT TESTED |
| (Z)-1-(3-Amino-4-methyl phenyl)-2-(3,4,5-trimethoxy phenyl)-ethene | 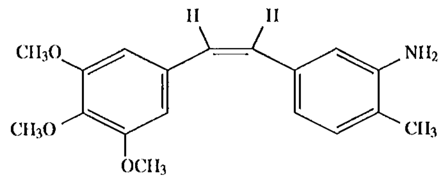 | 3.5 | 61.6[a), c)] (40 mg/day) |
| Combretastatin A-4 | | 0.2 | 4.6[a), d)] (40 mg/day) |
| (E)-3-(3-Amino-4-methoxy phenyl)-2-(3,4,5-trimethoxy phenyl)-prop-2-enenitrile | 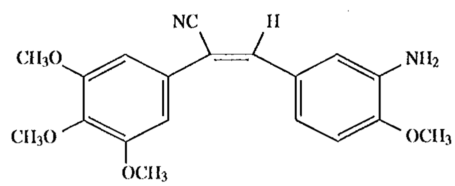 | 0.2 | 83.4[b), c)] 10 mg/day |
| (E)-3-(3-Amino-4-chloro phenyl)-2-(3,4,5-trimethoxy phenyl)-prop-2-enenitrile | 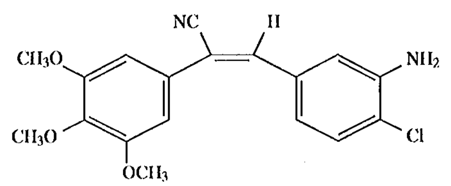 | 1.8 | 23.7[a), d)] (80 mg/day) |
| (E)-3-(3-Amino-4-methyl phenyl)-2-(3,4,5-trimethoxy phenyl)-prop-2-enenitrile | 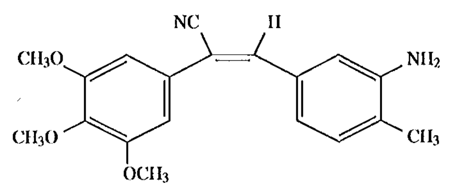 | 2.0 | 41.0[a), d)] 40 mg/day |
| Combretastatin A-4 | | 0.2 | 4.6[a), d)] (40 mg/day) | a) Administrated once a day on day 1, day 5 and day 7.
b) Administrated once a day from day 1 to day 10.
c) Administrated intravenously.
d) Administrated perorally.

EXAMPLE 9

Solubility

An excess amount of each sample was dissolved in 0.1 ml of phosphate buffer (PH 7.0). The mixture was sonicated and centrifuged. The supernatant was subjected to HPLC and the solubility was measured. The results obtained are shown in Table 2 below.

TABLE 2

| NAME OF COMPOUNDS | STRUCTURE | Solubility in Phosphate Buffer (PH 7.0)(mg/ml) |
|---|---|---|
| (Z)-1-(3-Amino-4-methoxy phenyl)-2-(3,4,5-trimethoxy phenyl)-ethene | 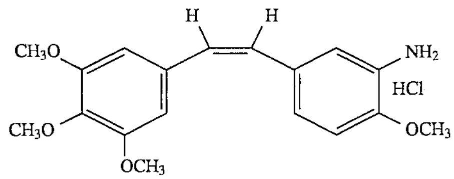 | 34 |
| (E)-3-(3-Amino-4-methoxy phenyl)-2-(3,4,5-trimethoxy phenyl-prop-2-enenitrile | 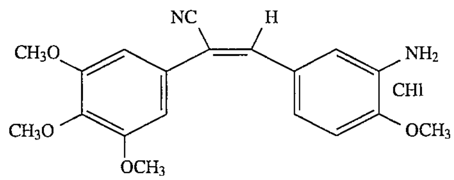 | 1.7 |
| Combretastatin A-4 | 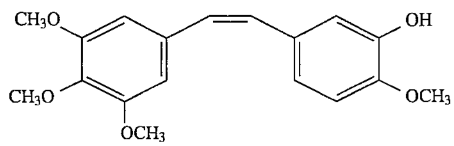 | <0.1 |

While the invention has been described in detail and in terms of specific embodiments thereof, it will be apparent to those skilled in the art that various modifications can be made therein without departing from the spirit and scope thereof.

What is claimed is:

1. A stilbene derivative of general formula (I) or a pharmaceutically acceptable acid addition salt thereof:

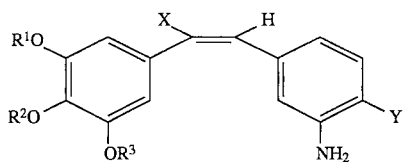

wherein $R^1$, $R^2$ and $R^3$, which may be the same or different, each represent an alkyl group having 1 to 3 carbon atoms; X represents a hydrogen atom or a nitrile group; Y represents an alkyloxy group having 1 to 3 carbon atoms or an alkyl group having 1 to 6 carbon atoms.

2. The stilbene derivative or pharmaceutically acceptable acid addition salt thereof according to claim 1 wherein $R^1$, $R^2$ and $R^3$ are each a methyl group.

3. The stilbene derivative or pharmaceutically acceptable acid addition salt thereof according to claim 1, wherein Y is a methoxy group.

4. The stilbene derivative or pharmaceutically acceptable acid addition salt thereof according to claim 1 having the formula

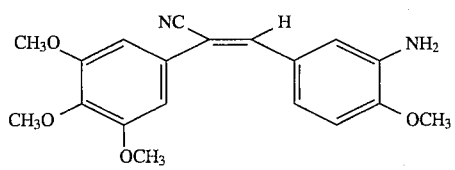

or a pharmaceutically acceptable acid addition salt thereof.

5. The stilbene derivative or pharmaceutically acceptable acid addition salt thereof according to claim 1 having the formula or a pharmaceutically acceptable acid addition salt thereof.

6. A pharmaceutical composition comprising a carcinostatically effective amount of a stilbene derivative or a pharmaceutically acceptable acid addition salt thereof according to claim 1 and a pharmaceutically acceptable excipient, diluent or carrier.

* * * * *